(12) United States Patent
Yu et al.

(10) Patent No.: US 8,338,628 B2
(45) Date of Patent: Dec. 25, 2012

(54) METHOD OF SYNTHESIZING ALKYLATED BILE ACID DERIVATIVES

(75) Inventors: Donna D. Yu, Arcadia, CA (US); Barry M. Forman, Irvine, CA (US)

(73) Assignee: City of Hope, Duarte, CA (US)

( * ) Notice: Subject to any disclaimer, the term of this patent is extended or adjusted under 35 U.S.C. 154(b) by 1225 days.

(21) Appl. No.: 12/125,499

(22) Filed: May 22, 2008

(65) Prior Publication Data

US 2009/0062526 A1    Mar. 5, 2009

Related U.S. Application Data

(60) Provisional application No. 60/968,534, filed on Aug. 28, 2007.

(51) Int. Cl.
*C07J 17/00* (2006.01)
*C07J 9/00* (2006.01)

(52) U.S. Cl. ........................................ 552/553; 540/118

(58) Field of Classification Search .................. 552/553; 540/118
See application file for complete search history.

(56) References Cited

U.S. PATENT DOCUMENTS 7,138,390 B2 * 11/2006 Pellicciari ..................... 514/182
7,786,102 B2 * 8/2010 Pellicciari ..................... 514/182
7,812,011 B2 * 10/2010 Pellicciari ..................... 514/182

FOREIGN PATENT DOCUMENTS

WO    WO2004/007521    *    1/2004

OTHER PUBLICATIONS

Forman, B. M., et al., "Identification of a Nuclear Receptor That is Activated by Farnesol Metabolites," Cell 81:687-693 (1995).

Lambert, G., et al., "The Farnesoid X-Receptor Is an Essential Regulator of Cholesterol Homeostasis," J. Biol. Chem. 278:2563-2570 (2003).
Makishima, M., et al., "Identification of a Nuclear Receptor for Bile Acids," Science 284:1362-1365 (1999).
Maloney, P. R., et al., "Identification of a Chemical Tool for the Orphan Nuclear Receptor FXR," J. Med. Chem. 43:2971-2974 (2000).
Miyashita, N., et al., "Pyridinium p-Toluenesulfonate. A Mild and Efficient Catalyst for the Tetrahydropyranylation of Alcohols," J. Org. Chem. 42:3772-3774 (1977).
Parks, D. J., et al., "Bile Acids: Natural Ligands for an Orphan Nuclear Receptor," Science 284:1365-1368 (1999).
Pellicciari, R., et al., "6Alpha-Ethyl-Chenodeoxycholic Acid (6-ECDCA), A Potent and Selective FXR Agonist Endowed with Anticholestatic Activity," J. Med. Chem. 45:3569-3572 (2002).
Pellicciari, R., et al., "Bile Acid Derivatives as Ligands of the Farnesoid X Receptor. Synthesis, Evaluation, and Structure-Activity Relationship of a Series of Body and Side Chain Modified Analogues of Chenodeoxycholic Acid," J. Med. Chem. 47:4559-4569 (2004).
Wang, H., et al., "Endogenous Bile Acids are Ligands for the Nuclear Receptor FXR/BAR," Mol. Cell 3:543-553 (1999).

* cited by examiner

*Primary Examiner* — Sabiha Qazi
(74) *Attorney, Agent, or Firm* — Perkins Coie LLP; Lauren Sliger

(57) ABSTRACT

A novel, improved method of synthesizing alkylated bile acid derivatives is provided. Such derivatives include, but are not limited to the active, potent, and selective FXR receptor agonist such as 6-ECDCA and other CA, DCA and CDCA derivatives. The first step of the synthesis selectively oxidates CDCA, CD, or DCA related starting material. An efficient combined deprotonation, trapping, ethylation, deprotection and reduction system is used to produce the desired alkylated bile acid derivatives. This practical synthesis offers a simple and economical pathway suitable for a large-scale manufacturing of alkylated bile acid derivatives including, but not limited to, 6-ECDCA.

4 Claims, 7 Drawing Sheets

$R_7$ = -OTHP if $R_1$ = -OH; $R_7$ = H if $R_1$ = H;
$R_8$ = -OTHP if $R_2$ = -OH; $R_8$ = H if $R_2$ = H.

A.

B.

METHOD OF SYNTHESIZING ALKYLATED BILE ACID DERIVATIVES

PRIORITY CLAIM

This application claims priority to U.S. Provisional Patent Application No. 60/968,534, filed Aug. 28, 2007, which is incorporated herein by reference.

FIELD OF THE INVENTION

The present invention relates to a novel, efficient method of synthesizing alkylated bile acid derivates, including but are not limited to 6-alkylated Chenodeoxycholic acid (CDCA) derivatives, 6-α-ethyl-CDCA (6-ECDCA), 6-alkylated cholic acid (CA) derivatives and 11-alkylated deoxycholic acid (DCA) derivatives, 6-ECDCA may also be referred to as 3α,7α-dihydroxy-6α-ethyl-5β-cholan-24-oic acid.

BACKGROUND

The farnesoid X receptor (FXR) is a nuclear hormone receptor that regulates gene expression in response to bile acids. FXR is important in the metabolism of bile acid, cholesterol, and lipoproteins. FXR agonists may be used in treating atherosclerosis, diabetes and cholestatic disease. Chenodeoxycholic acid (CDCA, FIG. 1) is a primary bile acid and among the most potent natural ligand of FXR with $EC_{50}$ values around 50 µM. Other bile acids, such as lithocholic acid, cholic acid (CA, FIG. 1) and deoxycholic acid (DCA, FIG. 1) also activate FXR, while ursodeoxycholic acid is inactive. The most potent synthetic non-steroidal FXR agonist, GW4064, has been identified through the use of high-throughput screening and combinatorial chemistry. Recent studies indicate that GW4064 activates FXR, increases HDL-cholesterol and reduces plasma triglycerides in vivo. However, GW4064 has very poor pharmacokinetic properties and is not useful clinically.

In a different approach, synthetic steroidal 6-ECDCA has recently been identified by traditional medicinal chemistry methods and found to be more potent with $EC_{50}$ values around 100 nM compared to the parent CDCA derivative and with improved pharmacokinetic properties relative to GW4064 (FIG. 1). Therefore, 6-ECDCA is a prime candidate for use in pharmacological therapy and as a tool to study the function of FXR. In existing methods for the preparation of 6-ECDCA, 7-keto-lithocholic acid, a very expensive starting material, is protected at the 3 position. The product is reacted with ethyl bromide under LDA to obtain the ethylating intermediate, followed by treatment with methanolic HCl under refluxed condition gave a methyl ester. Finally, selective reduction of methyl ester with sodium borohydride and subsequent hydrolysis of the methyl ester with NaOH in the methanol under refluxed condition to give 6-ECDCA in 3% yield for the synthesis of 6-ECDCA. Given the great promise of 6-ECDCA of a research tool and therapeutic molecule, a more efficient and less expensive methodology for the synthesis of this compound is needed. An efficient and economical methodology for the synthesis of similarly alkylated bile acid derivatives is also desired.

SUMMARY

A novel, economical, and efficient method of synthesizing alkylated bile acid derivatives is provided. The method comprises a selective oxidation of a bile acid starting material, followed by deprotonation, trapping, alkylation, deprotection and reduction to produce the desired bile acid derivatives. The method described herein is highly suitable for large-scale, industrial production.

One aspect of the invention is the synthesis of 6-substituted bile acid derivatives having the general formula I:

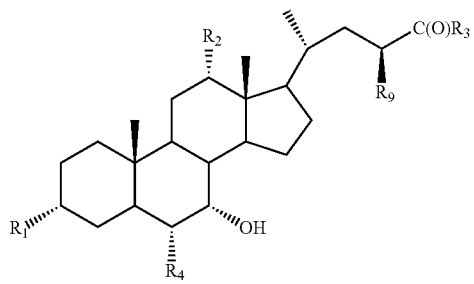

I wherein $R_1$, and $R_2$ are independently selected from the group consisting of hydrogen and hydroxyl group, but $R_1$ and $R_2$ cannot both be hydrogen simultaneously, $R_3$ is selected from the group consisting of hydroxyl and —$NR_5R_6$, wherein $R_5$ and $R_6$ are independently selected from the group consisting of hydrogen and alkyl groups, $R_4$ is selected from the group consisting of optionally substituted alkyl groups, wherein the substitution group is selected from the group consisting of hydroxyl, halogen, CN, and amide, and $R_9$ is methyl or hydrogen, from the corresponding bile acid starting material having the general formula II:

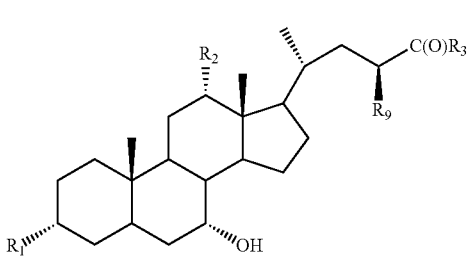

II wherein $R_1$, $R_2$, $R_3$ and $R_9$ are defined the same as in general formula I, following the synthesis route shown in FIG. 2B.

Another aspect of the invention is the synthesis of 6-substituted CDCA derivatives having the general formula CDCA-I:

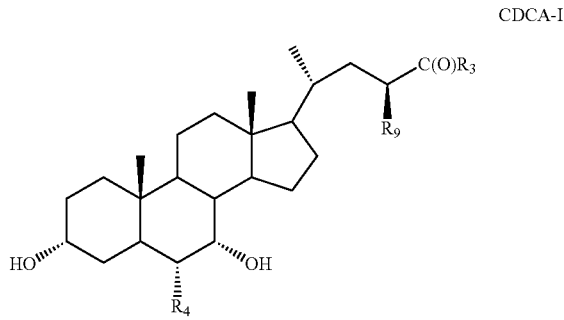

CDCA-I wherein $R_3$ is hydroxyl or $NR_5R_6$ wherein $R_5$ and $R_6$ are independently selected from the group consisting of hydrogen and alkyl group, $R_4$ is selected from the group consisting of optionally substituted alkyl groups, wherein the substitution group is selected from the group consisting of hydroxyl, halogen, CN, and amide, and $R_9$ is methyl or hydrogen, from the corresponding CDCA starting material having the general formula CDCA-II:

CDCA-II

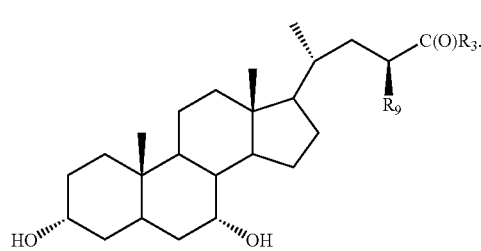

One example of the synthesis route is shown in FIG. 3B.

Another aspect of the invention is the synthesis of 6-substituted CA derivatives having the general formula CA-I:

CA-I

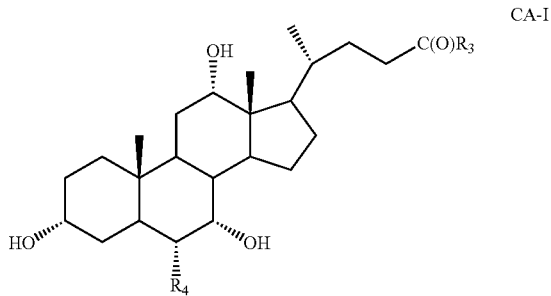

wherein $R_3$ is hydroxyl or $NR_5R_6$ wherein $R_5$ and $R_6$ are independently selected from the group consisting of hydrogen and alkyl group, from the corresponding CA starting material having the general formula CA-II:

CA-II

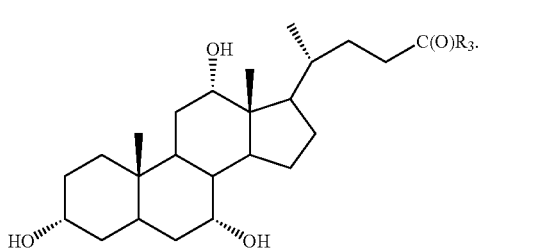

One example of the synthesis route is shown in FIG. 4B.

Another aspect of the invention is the synthesis of 11-substituted DCA derivative having the general formula DCA-I:

DCA-I

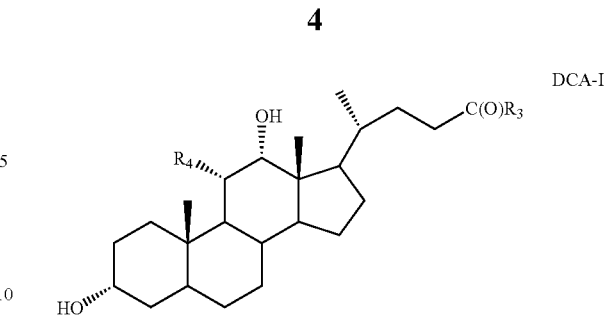

wherein $R_3$ is hydroxyl or $NR_5R_6$ wherein $R_5$ and $R_6$ are independently selected from the group consisting of hydrogen and alkyl group, from the corresponding DCA starting material having the general formula DCA-II:

DCA-II

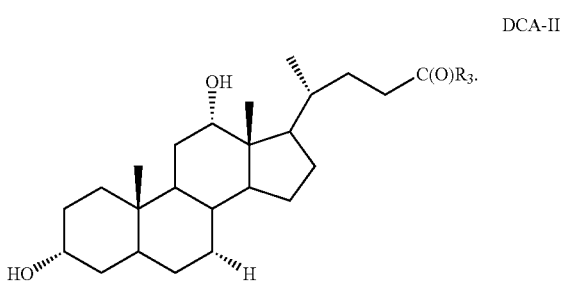

One example of the synthesis route is shown in FIG. 5B.

An additional aspect is the synthesis of 6-ECDCA from CDCA following the synthesis route shown in FIG. 6B. First, selective oxidization is used to convert CDCA by treatment with pyridinium chlorochromate (PCC) to 7-keto-lithochlic acid (FIG. 6B, compound 1) in good yields. The mechanism of selective oxidation with PCC is shown in FIG. 7. The initial oxidized reaction favored the formation of desired compound 7-keto in the first 15 minutes, but it was then converted to a dioxidized product with mono product 7-keto as a mixture after 15 minutes. In this procedure, 7-keto-monooxidized regional isomer is the majority, while the dioxidized in the 3 and 7-position product was detected in trace quantities. If the reaction was allowed to go longer, the mono-oxidized compound was not found in the 3-position. The mechanism of selective oxidation is due to steric hindrance of equatorial H bond in the 4-position. The PCC approaches from the equatorial direction the lower face of the 7-position and thus leads to the preferential formation in the 7-position of 7-keto.

Compound 1 was protected at the 3 position by treatment with 3,4-dihydro-2H-pyran in the combination of $CHCl_3/Cl_2CH_2$/Ether in the presence of catalytic amount of p-toluenesulfonic acid to give the corresponding 3-tetrahydropyranyloxy (FIG. 6B, compound 2). Treatment of compound 2 with lithium diisopropylamide (LDA)/hexamethylphosphoramide (HMPA) and ethyl iodine followed by pyridinium p-toluenesulfonate (PPTS) for the deprotection of tetrahydropyranyl (THP) group in the 3-position provided intermediate compound 3 of FIG. 6B. Selective reduction of 3 with sodium borohydride ($NaBH_4$) gave desired compound 4 (6-ECDCA) of FIGS. 6A and 6B.

DETAILED DESCRIPTION

Figure 1:
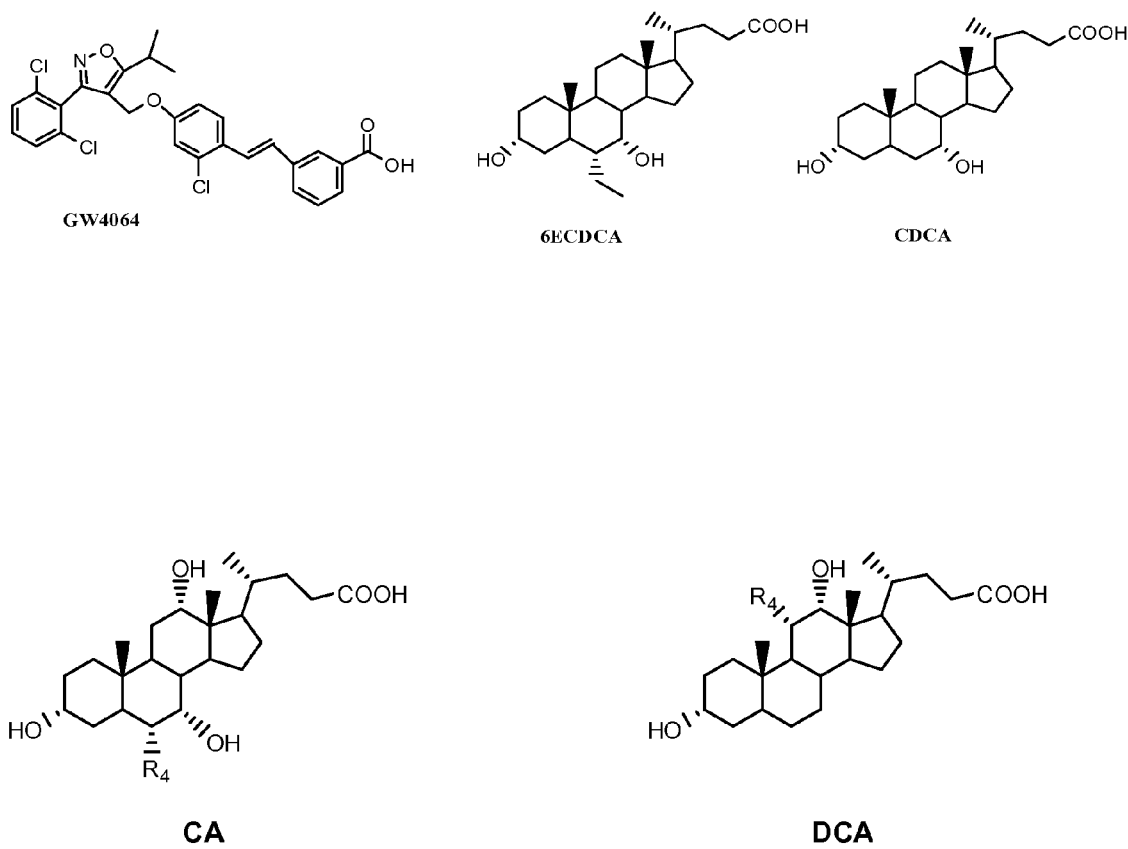
FIG. 1 is the chemical structures of GW4064, 6-ECDCA, CDCA, CA, and DCA which are known natural and synthetic ligands of FXR.
Figure 2:
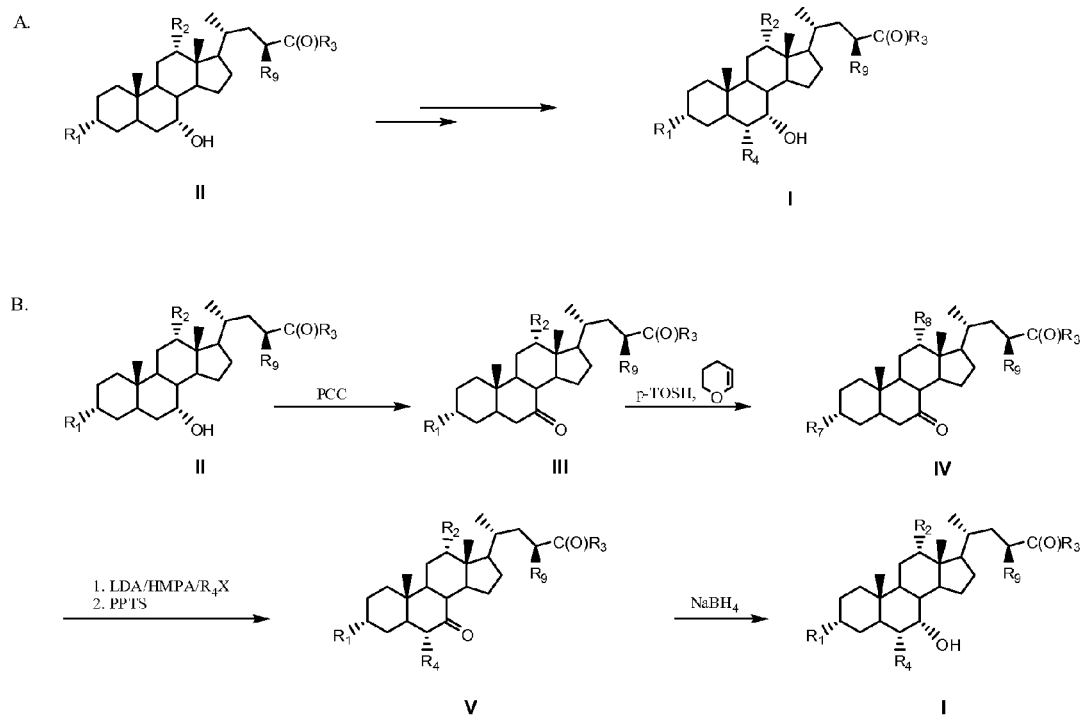
FIG. 2A shows the bile acid starting material having general formula II and the resultant 6-alkylated bile acid derivative having general formula I after the novel synthesis method is applied.
FIG. 2B shows the bile acid starting material having general formula II and the intermediate compounds created utilizing one aspect of the present method to synthesize the alkylated bile acid derivative having general formula I.
Figure 3:
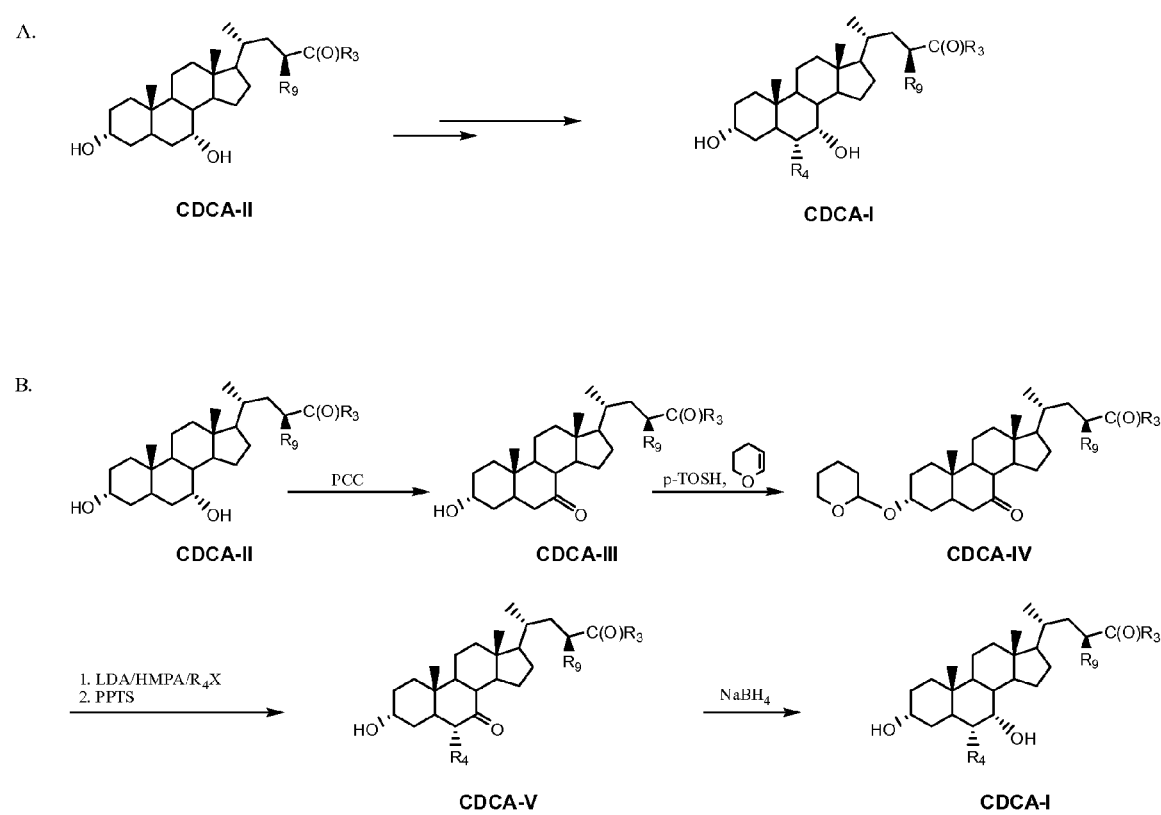
FIG. 3A shows the CDCA starting material having general formula CDCA-II and the resultant alkylated bile acid derivative having general formula CDCA-I after the novel synthesis method is applied.
FIG. 3B shows the bile acid starting material having general formula CDCA-II and the intermediate compounds created utilizing one aspect of the present method to synthesize the alkylated bile acid derivative having general formula CDCA-I.
Figure 4:
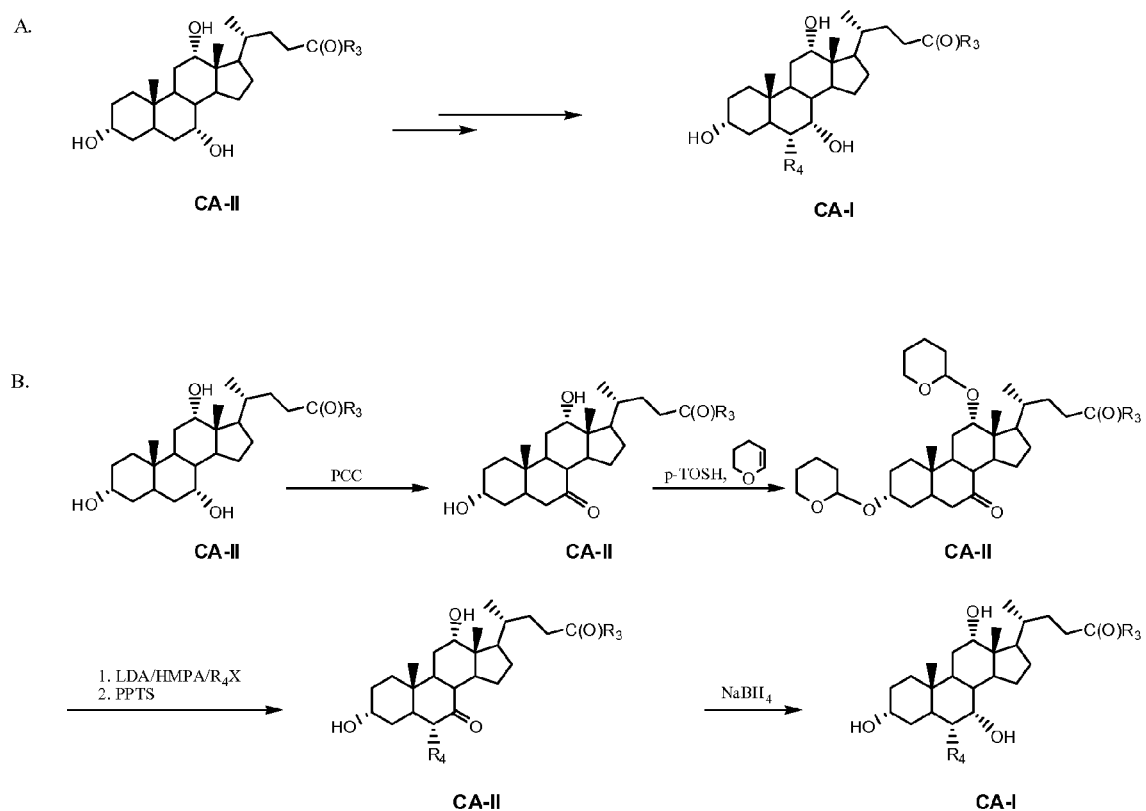
FIG. 4A shows the CA starting material having general formula CA-II and the resultant alkylated bile acid derivative having general formula CA-I after the novel synthesis method is applied.
FIG. 4B shows the bile acid starting material having general formula CA-II and the intermediate compounds created utilizing one aspect of the present method to synthesize the alkylated bile acid derivative having general formula CA-I.
Figure 5:
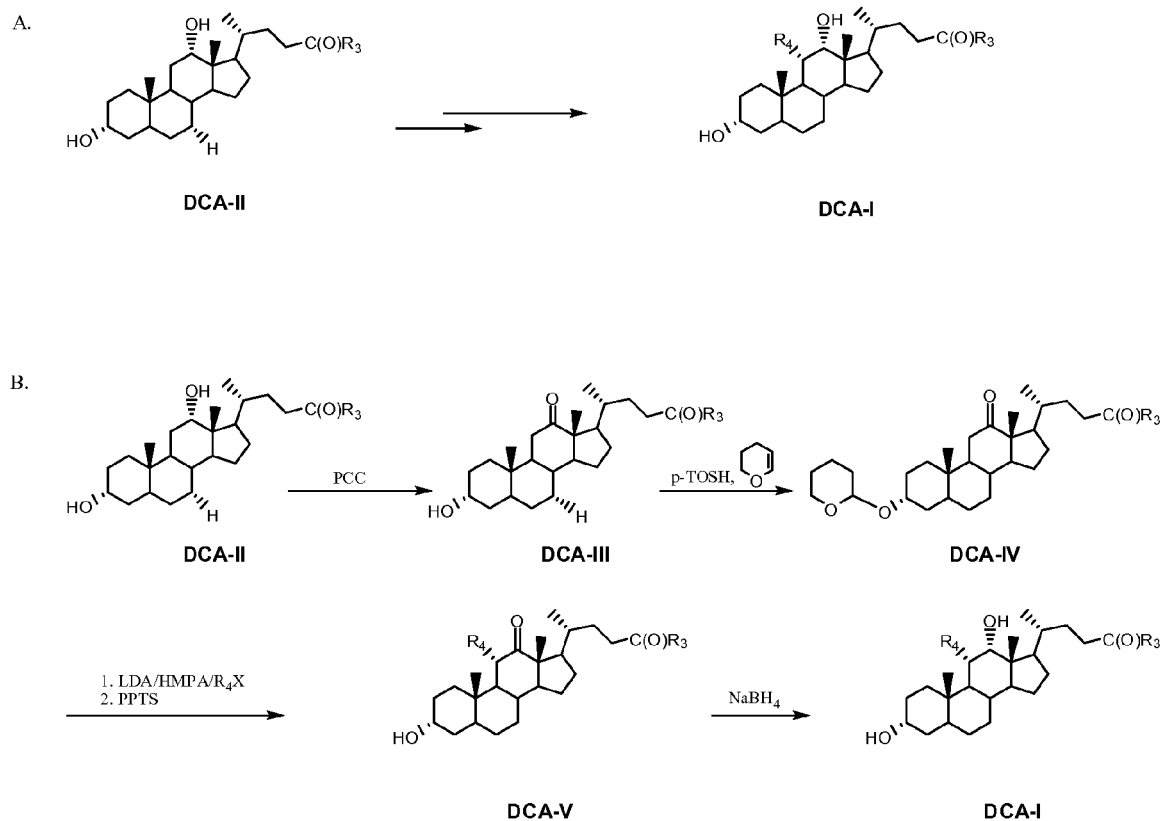
FIG. 5A shows the DCA starting material having general formula DCA-II and the resultant alkylated bile acid derivative having general formula DCA-I after the novel synthesis method is applied.
FIG. 5B shows the bile acid starting material having general formula DCA-II and the intermediate compounds created utilizing one aspect of the present method to synthesize the alkylated bile acid derivative having general formula DCA-I.
Figure 6:
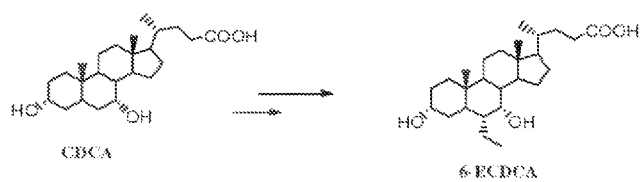
FIG. 6A shows the CDCA starting material and the resultant 6-ECDCA after the novel synthesis method is applied.
FIG. 6B shows the CDCA and the intermediate compounds created utilizing one aspect of the present method to synthesize 6-ECDCA.
Figure 6:
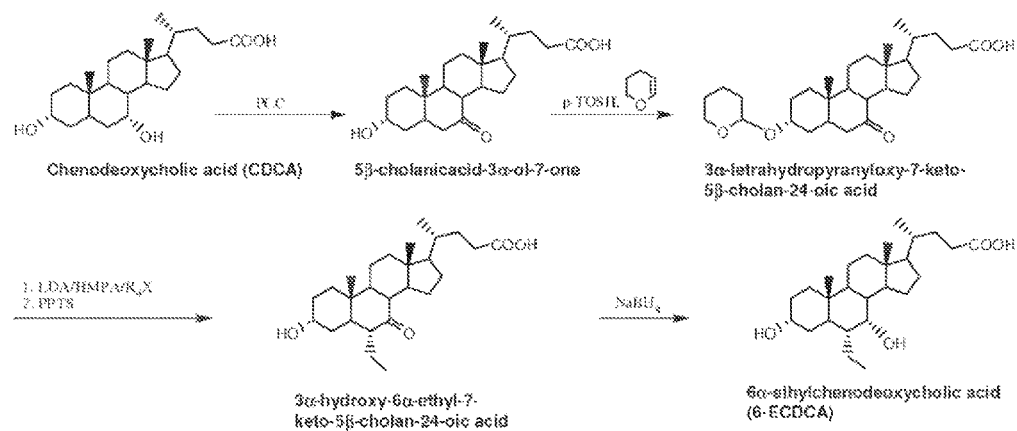
Figure 7:
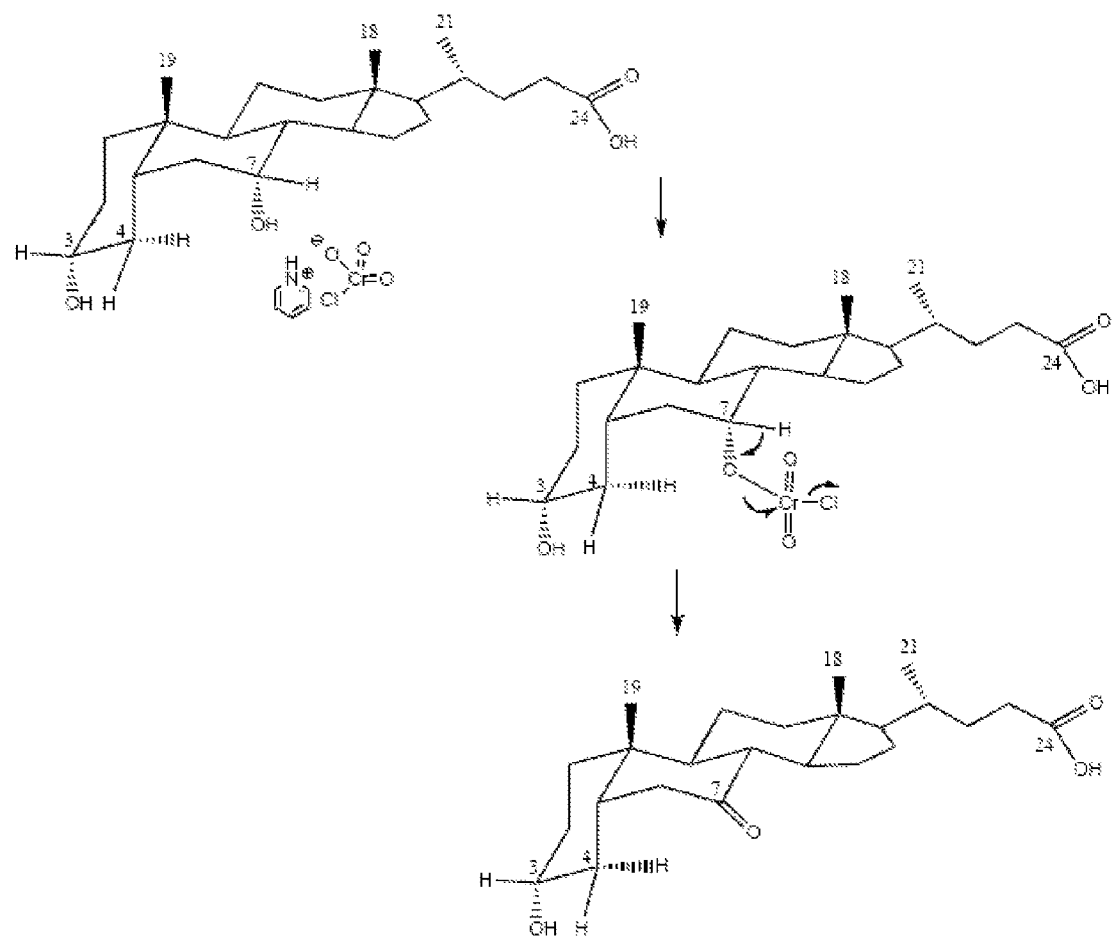
FIG. 7 is a depiction of the mechanism of the selective oxidation with PCC illustrated in the 7-oxidation of CDCA.

The first step of the novel synthesis route is a selective oxidation of the bile acid starting material by pyridinium chlorochromate (PCC), whose mechanism is depicted in FIG. 7 as in the 7-oxidation of CDCA. The remaining hydroxyl groups in the resultant oxidated bile acid derivative are protected. One example of such alcohol protection can be accomplished by tetrahydropyranylation using conventional organic synthesis methods. The desired alkylation occurs at the alpha carbon adjacent to the carbonyl group using alkyl halide following conventional organic synthesis methods. Examples of deprotonation agent include, but are not limited to LDA and n-BuLi. The tetrahydropyranyl groups are removed using conventional organic synthesis method. One method to remove the tetrahydropyranyl groups uses pyridinium p-toluenesulfonate (PPTS) following the method reported in Miyashita et al. Finally the carbonyl group is reduced alcohol. The reduction reaction may be achieved with $NaBH_4$ using conventional organic chemistry.

The yield for the inventive synthesis of 6-ECDCA is at least 9%. More preferably, the yield of the inventive synthesis is at least 20%, at least 30%, at least 40%, at least 50%, or at least 75%.

"Large scale production" means production of the desired alkylated bile acid derivative such as 6-ECDCA in amounts of about 0.25 kilograms or greater, preferably about 0.5 kilograms or greater, and more preferably about 1.0 kilogram or greater, e.g., multi-kilograms.

"Alkylation" means substituting a molecule with an alkyl group.

"Alkyl group" means optionally substituted saturated or unsaturated C1-C10 alkyl group.

"Optionally substituted" means no substitution or substitution selected from the group consisting of halogen, CN, hydroxyl, and amide.

General Procedures.

Organic reagents were purchased from commercial suppliers unless otherwise noted and were used without further purification. All solvents were analytical or reagent grade. All reactions were carried out in flame-dried glassware under argon or nitrogen. Melting points were determined and reported automatically by an optoelectronic sensor in open capillary tubes and were uncorrected. $^1H$ NMR and $^{13}C$ NMR spectra were measured at 500 MHz and 125 MHz respectively, and using $CDCl_3$ or $CD_3OD$ as the solvents and tetramethylsilane ($Me_4Si$) as the internal standard. Flash column chromatography was performed using Sigma-Aldrich silica gel 60 (200-400 mesh), carried out under moderate pressure by using columns of an appropriate size packed and eluted with appropriate eluents. All reactions were monitored by TLC on precoated plates (silica gel HLF). TLC spots were visualized either by exposure to iodine vapors or by irradiation with UV light. Organic solvents were removed in vacuum by rotary evaporator. Elemental analyses were performed by Desert Analytics, Tucson, Ariz.

Synthesis of 5β-Cholanicacid-3α-ol-7-one (Compound 1). To a suspension solution of chenodeoxycholic acid (CDCA) (1.0 g, 0.0025 mol) and silica gel (4 g, 200-400 mesh, Aldrich) in anhydrous $CHCl_3$ (2 mL), $CH_2Cl_2$ (25 mL) was added pyridinium chlorochromate (0.81 g, 0.038 mol) in portions and the reaction mixture was stirred at room temperature for 15 min. The mixture was filtered and the filtrate was washed with water (20 mL) and brine (20 ml). The organic layer was dried over $Na_2SO_4$ and concentrated. The crude oil was purified by flash column chromatography ($CH_2Cl_2$/MeOH 95:5) to produce 1 as a solid (0.76 g, in 78% yield), mp: 201.1° C. (lit.[1] mp: 203-204° C.). $^1H$ NMR ($CD_3OD$) δ 3.50 (m, 1H), 2.94 (m, 1H), 2.52 (t, 1H), 2.30 (m, 2H), 2.19 (m, 6H), 1.70 (m, 2H), 1.43 (m, 4H), 1.31 (m, 6H), 1.19 (s, 3H), 1.12 (m, 4H), 0.92 (d, 3H), 0.67 (s, 3H). $^{13}C$ NMR ($CD_3OD$) δ 213.7, 176.8, 70.1, 54.8, 49.2, 48.9, 47.7, 46.0, 44.9, 43.0, 42.4, 38.9, 36.8, 35.1, 34.9, 33.7, 31.0, 30.6, 29.2, 27.8, 24.3, 22.0, 21.4, 17.3, 10.5. Anal. Calcd for $C_{24}H_{38}O_4$: C, 73.81; H, 9.81. Found: C, 73.50; H, 9.63.

Synthesizing 3α-Tetrahydropyranyloxy-7-keto-5β-cholan-24-oic acid (Compound 2). To a solution of 5β-cholanicacid-3α-ol-7-one (1) (0.5 g, 0.0013 mol) in $CHCl_3/Cl_2CH_2$/Ether (1:1:2, 16 mL), p-toluensulfonic acid (0.06 g, 0.0003 mol), and 3,4-dihydro-2H-pyrane (0.41 g, 0.005 mol) were added. The reaction mixture was stirred at room temperature for 60 min and water (10 mL) was added. The reaction mixture was extracted with EtOAc (3×30 ml) and washed with saturated NaHCO$_3$ and brine. After concentration to remove solvent, the crude oil was purified by flash column chromatography (CH$_2$Cl$_2$/Ether 1:2) to produce 2 as a white solid (0.47 g. in 76% yield), mp: 160.8° C. (lit.[1] mp: 157-159° C.). $^1$H NMR (CDCl$_3$) δ 4.73 (d, 1H), 3.86 (m, 1H), 3.59 (m, 1H), 3.46 (m, 1H), 2.82 (m, 1H), 1.17 (s, 3H), 0.92 (d, 3H), 0.63 (s, 3H). $^{13}$C NMR (CDCl$_3$) δ 212.3, 179.8, 96.4, 62.8, 62.1, 19.8, 18.1, 11.4. Anal. Calcd for C$_{29}$H$_{46}$O$_5$: C, 73.38; H, 9.77. Found: C, 73.30; H, 9.76.

Synthesizing 3α-Hydroxy-6α-ethyl-7-keto-5β-cholan-24-oic acid (Compound 3). To a solution of 3α-tetrahydropyranyloxy-7-keto-5β-cholan-24-oic acid (2) (0.3 g, 0.00063 mol) and HMPA (0.7 g, 0.004 mol) in dry THF (20 mL), LDA (1.8 M in tetrahydrofuran/heptane/ethylbenzene) (2.0 mL, 0.0036 mol) was added dropwise at −78° C. The reaction mixture was stirred for 30 min. Ethyl iodide (2.0 g, 0.013 mol) was slowly added and the reaction mixture was allowed to warm overnight to room temperature. After concentration to remove solvent, water and ether was added. The reaction mixture was acidified with 10% HCl, extracted with EtOAc (5×20 mL), washed with brine, dried over Na$_2$SO$_4$, and concentrated to give yellow oil. After a short column by CH$_2$Cl$_2$/Ether 1:2, the crude semi-solid was dissolved in chloroform (5 mL) and PPTS (0.015 g, 0.00006 mol) was added. The reaction mixture was stirred at 55° C. for 7 h. The solvent was evaporated in vacuo, the crude semi-solid (0.08 g) was obtained through a quick column and was passed to the next step without further purification.

Synthesizing 3α,7α-Dihydroxy-6α-ethyl-5β-cholan-24-oic acid (6-ECDCA) (Compound 4: Desired End Product). To a solution of 3α-hydroxy-6α-ethyl-7-keto-5β-cholan-24-oic acid (3). (0.05 g, 0.00012 mol) in dry MeOH (5 mL), NaBH$_4$ (0.03 g, 0.00084 mol) was added in a small portion at 0° C. The reaction mixture was stirred at room temperature for 3 hr. H$_2$O (10 mL) was slowly added. The reaction mixture was partially concentrated to remove solvent and extracted with EtOAc (3×20 mL). The combined organic extracts were washed with brine, dried over Na$_2$SO$_4$, and concentrated to give a solid. The crude product was purified by flash column chromatography (CH$_2$Cl$_2$/Ether 1:2) to give the desired product 0.04 g in 80% yield. $^1$H NMR (CDCl$_3$) δ 3.65 (brs, 1H), 3.31 (m, 1H), 2.33 (m, 1H), 2.20 (m, 1 h), 0.97 (d, 3H), 0.89 (m, 6H), 0.69 (s, 3H). $^{13}$C NMR (CDCl$_3$) δ 177.0, 71.8, 69.7, 55.9, 50.2, 45.5, 42.3, 41.7, 40.1, 39.6, 35.3, 35.2, 33.1, 33.0, 31.0, 29.8, 27.8, 23.1, 22.3, 22.1, 20.5, 17.3, 11.0, 10.6. Anal. Calcd for C$_{26}$H$_{44}$O$_4$.¼H$_2$O: C, 73.44; H, 10.43. Found: C, 73.24; H, 10.66.

Synthesis of 6-modified CDCA derivative having the general formula CDCA-I from CDCA starting material having the general formula CDCA-I. To a suspension solution of CDCA-II (0.0025 mol) and silica gel (4 g, 200-400 mesh, Aldrich) in anhydrous CHCl$_3$ (2 mL), CH$_2$Cl$_2$ (25 mL) is added pyridinium chlorochromate (0.81 g, 0.038 mol) in portions and the reaction mixture is stirred at room temperature for 15 min. The mixture is filtered and the filtrate is washed with water (20 mL) and brine (20 ml). The organic layer is dried over Na$_2$SO$_4$ and concentrated to a crude product. The crude product is purified by flash column chromatography to produce a product having the general formula CDCA-III.

To a solution of CDCA-III (0.0013 mol) in CHCl$_3$/Cl$_2$CH$_2$/Ether (1:1:2, 16 mL), p-toluensulfonic acid (0.06 g, 0.0003 mol), and 3,4-dihydro-2H-pyrane (0.41 g, 0.005 mol) are added. The reaction mixture is stirred at room temperature for 60 min, and water (10 mL) is added. The reaction mixture is extracted with EtOAc (3×30 ml) and washed with saturated NaHCO$_3$ and brine. After concentration to remove solvent, the crude product is purified by flash column chromatography to produce a compound having the general formula CDCA-IV.

To a solution of CDCA-IV (0.00063 mol) and HMPA (0.7 g, 0.004 mol) in dry THF (20 mL), LDA (1.8 M in tetrahydrofuran/heptane/ethylbenzene) (2.0 mL, 0.0036 mol) is added dropwise at −78° C. The reaction mixture is stirred for 30 min. The corresponding alkyl halide R$_4$—X (0.013 mol) is slowly added and the reaction mixture is allowed to warm overnight to room temperature. After concentration to remove solvent, water and ether is added. The reaction mixture is acidified with 10% HCl extracted with EtOAc (5×20 mL), washed with brine, dried over Na$_2$SO$_4$, and concentrated to give a crude product. After a short column, the crude product is dissolved in chloroform (5 mL), and PPTS (0.015 g, 0.00006 mol) is added. The reaction mixture is stirred at 55° C. for 7 hours. The solvent is evaporated in vacuo. The crude product having the general formula of CDCA-V is obtained through a quick column and passed to the next step without further purification.

To a solution of CDCA-V (0.00012 mol) in dry MeOH (5 mL), NaBH$_4$ (0.03 g, 0.00084 mol) is added in a small portion at 0° C. The reaction mixture is stirred at room temperature for 3 hours as water (10 mL) is slowly added. The reaction mixture is partially concentrated to remove solvent and extracted with EtOAc (3×20 mL). The combined organic extracts are washed with brine, dried over Na$_2$SO$_4$, and concentrated to give a crude product. The crude product is purified by flash column chromatography to give the desired alkylated product having the general formula of CDCA-I.

Synthesis of 6-modified CA derivative having the general formula CA-I from CA starting material having the general formula CA-II. To a suspension solution of CA-II (0.0025 mol) and silica gel (4 g, 200-400 mesh, Aldrich) in anhydrous CHCl$_3$ (2 mL), CH$_2$Cl$_2$ (25 mL) is added pyridinium chlorochromate (0.81 g, 0.038 mol) in portions and the reaction mixture is stirred at room temperature for 15 min. The mixture is filtered and the filtrate is washed with water (20 mL) and brine (20 ml). The organic layer is dried over Na$_2$SO$_4$ and concentrated. The crude product is purified by flash column chromatography to produce a product having the general formula of CA-III.

To a solution of CA-III (0.0013 mol) in CHCl$_3$/Cl$_2$CH$_2$/Ether (1:1:2, 16 mL), p-toluensulfonic acid (0.06 g, 0.0003 mol), and 3,4-dihydro-2H-pyrane (0.41 g, 0.005 mol) are added. The reaction mixture is stirred at room temperature for 60 min and water (10 mL) is added. The reaction mixture is extracted with EtOAc (3×30 ml) and washed with saturated NaHCO$_3$ and brine. After concentration to remove solvent, the crude product is purified by flash column chromatography to produce compound having the general formula of CA-IV.

To a solution of CA-IV (0.00063 mol) and HMPA (0.7 g, 0.004 mol) in dry THF (20 mL), LDA (1.8 M in tetrahydrofuran/heptane/ethylbenzene) (2.0 mL, 0.0036 mol) is added dropwise at −78° C. The reaction mixture is stirred for 30 min. The corresponding alkyl halide $R_4$—X (0.013 mol) is slowly added and the reaction mixture is allowed to warm overnight to room temperature. After concentration to remove solvent, water and ether is added. The reaction mixture is acidified with 10% HCl, extracted with EtOAc (5×20 mL), washed with brine, dried over $Na_2SO_4$, and concentrated to give a crude product. After a short column, the crude product is dissolved in chloroform (5 mL) and PPTS (0.015 g, 0.00006 mol) is added. The reaction mixture is stirred at 55° C. for 7 h. The solvent is evaporated in vacuo. The crude product having the general formula CA-V is obtained through a quick column and passed to the next step without further purification.

To a solution of CA-V (0.00012 mol) in dry MeOH (5 mL), $NaBH_4$ (0.03 g, 0.00084 mol) is added in a small portion at 0° C. The reaction mixture is stirred at room temperature for 3 hr. $H_2O$ (10 mL) is slowly added. The reaction mixture is partially concentrated to remove solvent and extracted with EtOAc (3×20 mL). The combined organic extracts are washed with brine, dried over $Na_2SO_4$, and concentrated to give a crude product. The crude product is purified by flash column chromatography to give a desired 6-alkylated CA derivative having the general formula of CA-I.

Synthesis of 11-modified DCA derivative having the general formula of DCA-I from DCA starting material having the general formula of DCA-I. To a suspension solution of a compound having the general formula of DCA-II (0.0025 mol) and silica gel (4 g, 200-400 mesh, Aldrich) in anhydrous $CHCl_3$ (2 mL) and $CH_2Cl_2$ (25 mL) is added pyridinium chlorochromate (0.81 g, 0.038 mol) in portions. The reaction mixture is stirred at room temperature for 15 min. The mixture is filtered and the filtrate is washed with water (20 mL) and brine (20 ml). The organic layer is dried over $Na_2SO_4$ and concentrated. The crude product is purified by flash column chromatography to produce a compound having the general formula of DCA-III, To a solution of DCA-III (0.0013 mol) in $CHCl_3/Cl_2CH_2$/Ether (1:1:2, 16 mL), p-toluensulfonic acid (0.06 g, 0.0003 mol), and 3,4-dihydro-2H-pyrane (0.41 g, 0.005 mol) are added. The reaction mixture is stirred at room temperature for 60 min and water (10 mL) is added. The reaction mixture is extracted with EtOAc (3×30 ml) and washed with saturated $NaHCO_3$ and brine. After concentration to remove solvent, the crude product is purified by flash column chromatography to produce a compound having the general formula of DCA-IV.

To a solution of DCA-IV (0.00063 mol) and HMPA (0.7 g, 0.004 mol) in dry THF (20 mL), LDA (1.8 M in tetrahydrofuran/heptane/ethylbenzene) (2.0 mL, 0.0036 mol) is added dropwise at −78° C. The reaction mixture is stirred for 30 min. The corresponding alkyl halide $R_4$—X (0.013 mol) is slowly added and the reaction mixture is allowed to warm overnight to room temperature. After concentration to remove solvent, water and ether is added. The reaction mixture is acidified with 10% HCl, extracted with EtOAc (5×20 mL), washed with brine, dried over $Na_2SO_4$, and concentrated to give a crude product. After a short column, the crude product is dissolved in chloroform (5 mL) and PPTS (0.015 g, 0.00006 mol) is added. The reaction mixture is stirred at 55° C. for 7 h. The solvent is evaporated in vacuo. The obtained crude compound having the general formula of DCA-V is obtained through a quick column and is passed to the next step without further purification.

To a solution of DCA-V (0.00012 mol) in dry MeOH (5 mL), $NaBH_4$ (0.03 g, 0.00084 mol) is added in a small portion at 0° C. The reaction mixture is stirred at room temperature for 3 hr. $H_2O$ (10 mL) is slowly added. The reaction mixture is partially concentrated to remove solvent and then extracted with EtOAc (3×20 mL). The combined organic extracts are washed with brine, dried over $Na_2SO_4$, and concentrated to give a crude product. The crude product is purified by flash column chromatography to give a desired 11-alkylated DCA derivative having the general formula of DCA-I.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein. Additionally, all publications are incorporated by reference in their entirety.

REFERENCES

1. Forman, B. M., E. Goode, J. Chen, A. E. Oro, D. J. Bradley, T. Perlman, D. J. Noonan, L. T. Burka, T. McMorris, W. W. Lamph, R. M. Evans, and C. W. Weinberger. 1995. Identification of a nuclear receptor that is activator by farnesol metabolites, Cell 81, 687-693.
2. Wang, H., J. Chen, K. Hollister, L. C. Sower, and B. M. Forman. 1999. Endogenous bile acids are ligands for the nuclear receptor FXR/BAR, Mol. Cell 3, 543-553.
3. Makishima, M., A. Y. Okamoto, J. J. Repa, H. Tu, R. M. Learned, A. Luk, M. V. Hull, K. D. Lustig, and D. J. Mangelsdorf. 1999. Identification of a nuclear receptor for bile acids, Science 284, 1362-1365.
4. Parks, D. J., S. G. Blanchard, R. K. Bledsoe, G. Chandra, T. G. Consler, S. A. Kliewer, J. B. Stimmel, T. M. Wilson, A. M. Zavacki, D. D. Moore, and J. M. Lehmann. 1999. Bile acids: natural ligands for an orphan receptor, Science 284, 1365-1368.
5. Willson, T. M., S. A. Jones, J. T. Moore, and S. A. Kliewer. 2001. Chemical genomics: functional analysis of orphan nuclear receptors in the regulation of bile acid metabolism, Med. Res. Rev. 21, 513-522.
6. Lambert, G., Amar, M. J., Guo, G., Brewer H. B. Jr., Gonzalez, F. J., Sinal, C. J. 2002. The Farnesoid X-receptor is an essential regulator of cholesterol homeostasis, J. Biol. Chem. epub ahead of print.
7. Maloney, P. R., D. J. Parks, C. D. Haffner, A. M. Fivush, G. Chandra, K. D. Plunket, K. L. Greech, P. R. Moore, J. G. Wilson, M. C. Lewis, S. A. Jones, and T. M. Willson. 2000. Identification of a chemical tool for the orphan nuclear receptor FXR, J. Med. Chem. 2000, 43, 2971-2974.
8. Pellicciari, R.; Costantino, G. Camaioni, E.; Clerici, C.; Sadeghpour, B. M.; Entrena, A.; Willson, T. M; Fiorucci, S.; Clerici, C.; Gioiello, A. Bile Acid Derivatives as Ligands of the Farnesoid X Receptor. Synthesis, Evaluation, and Structure-Activity Relationship of a Series of Body and side Chain Modified Analogues of Chenodeoxycholic Acid. J. Med. Chem. 2004, 47, 4559-4569.
9. Pellicciari, R.; Fiuorucci, S.; Camaioni, E.; Clerici, C.; Costantino, G.; Maloney, P. R.; Morelli, A.; Parks, D. J.; Willson, T. M. 6☐-Ethyl-chenodeoxycholic acid (6-ECDCA), a potent and selective FXR agonist endowed with anticholestatic activity. J. Med. Chem. 2002, 45, 3569-3572.
10. Miyashita, N; Yoshkoshi, A; Grieco, P. A. Pyridinium p-Toluenesulfonate. A mild and Efficient Catalyst for the Tetrahydropyranylation of Alcohols. J. Org. Chem. 1977, 426, 3772-3774.

The invention claimed is:

1. A method for producing 6α-ethylchenodeoxycholic acid (6-ECDCA) from chenodeoxycholic acid (CDCA) comprising the following steps:
   (i) oxidizing CDCA with pyridinium chlorochromate (PCC) to produce 5β-cholanicacid-3α-ol-7-one

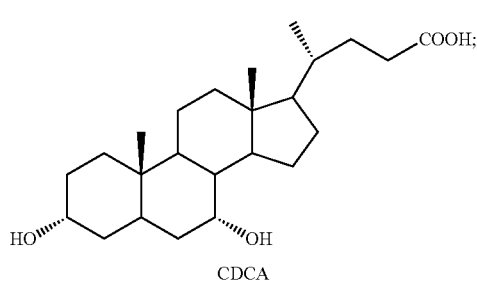

CDCA (ii) contacting a solution of 5β-cholanicacid-3α-ol-7-one with (a) 3,4-dihydro-2H-pyran and (b) p-toluenesulfonic acid to result 3α-tetrahydropyranyloxy-7-keto-5β-cholan-24-oic acid;
(iii) contacting a solution of 3α-tetrahydropyranyloxy-7-keto-5β-cholan-24-oic acid with ethyl iodine to produce 3α-tetrahydropyranyloxy-6α-ethyl-7-keto-5β-cholan-24-oic acid;
(iv) contacting 3α-tetrahydropyranyloxy-6α-ethyl-7-keto-5β-cholan-24-oic acid with pyridinium p-toluenesulfonate (PPTS) to result 3α-hydroxy-6α-ethyl-7-keto-5β-cholan-24-oic acid; and
(v) reducing 3α-hydroxy-6α-ethyl-7-keto-5β-cholan-24-oic acid with $NaBH_4$ to produce 6-ECDCA

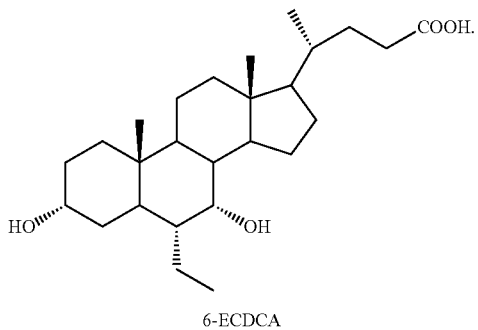

6-ECDCA

2. The method of claim 1, wherein the method is used for large scale production.

3. The method of claim 1, wherein the method yields at least 20% 6-ECDCA.

4. The method of claim 1, wherein the method yields at least 50% 6-ECDCA.

* * * * *